United States Patent [19]

Hughes

[11] Patent Number: 5,277,191
[45] Date of Patent: Jan. 11, 1994

[54] HEATED CATHETER FOR MONITORING CARDIAC OUTPUT

[75] Inventor: Timothy J. Hughes, Palo Alto, Calif.

[73] Assignee: Abbott Laboratories, Abbott Park, Ill.

[21] Appl. No.: 717,549

[22] Filed: Jun. 19, 1991

[51] Int. Cl.$^5$ .......................................... A61B 5/028
[52] U.S. Cl. .................................. 128/713; 128/692
[58] Field of Search ............... 128/713, 692, 670, 671, 128/642, 401; 73/204.16, 204.17, 204.18, 204.19

[56] References Cited

U.S. PATENT DOCUMENTS

| | | | |
|---|---|---|---|
| 3,085,431 | 4/1963 | Yerman et al. | 73/204.16 |
| 3,359,974 | 12/1967 | Khalil | 128/713 |
| 4,217,910 | 8/1980 | Khalil | 128/713 |
| 4,450,719 | 5/1984 | Nishimura et al. | 73/204.17 X |
| 4,679,561 | 7/1987 | Doss | 128/401 |
| 4,955,377 | 9/1990 | Lennox et al. | 128/401 |
| 4,979,948 | 12/1990 | Geddes et al. | 128/401 |
| 5,035,514 | 7/1991 | Newman | 73/204.19 |
| 5,056,526 | 10/1991 | Khalil | 128/692 |
| 5,106,360 | 4/1992 | Ishiwara et al. | 128/401 |
| 5,122,137 | 6/1992 | Lennox | 128/401 |

FOREIGN PATENT DOCUMENTS 1108331  8/1984  U.S.S.R. .......................... 73/204.16

OTHER PUBLICATIONS

A. L. Delaunois "Thermal method for continuous blood-velocity measurements in large blood vessels and cardiac-output determination" Mar. 1973, vol. 11 from Medical & Biological Engineering pp. 201-205.

Primary Examiner—William E. Kamm
Assistant Examiner—Samuel Gilbert
Attorney, Agent, or Firm—Christensen, O'Connor, Johnson & Kindness

[57] ABSTRACT

A heated catheter for monitoring cardiac output. Displaced from a distal end of a heated catheter (30) is a resistive heater (32) that heats blood flowing within a heart muscle (10). The resistive heater is mounted on the catheter so that when the catheter is inserted into the heart, the resistive heater is disposed in the right ventricle. A temperature sensor (34) is disposed downstream of the resistive heater, in or proximate the pulmonary artery during use. A differential amplifier (40, 70) provides an electrical current to the resistive heater that varies as a function of the difference between the temperature of the resistive heater, measured by a temperature sensor (35), and a predetermined temperature. In another embodiment of the invention, a resistive heater (90) has a resistance that varies with temperature. The resistive heater comprises one arm of a bridge circuit (85). A differential amplifier (110) provides an electrical current to the bridge circuit in response to the voltage developed across the bridge circuit. In yet another embodiment, a constant power dissipation is maintained in a resistive heater (60), so long as its temperature does not exceed a predetermined maximum. Should that occur, a power control block (80) incrementally reduces the power dissipated in the resistive heater, thereby insuring that the temperature of the resistive heater does not damage blood cells, yet is sufficient to provide a good signal-to-noise ratio in respect to a signal indicative of the temperature rise in blood flowing from the heart.

18 Claims, 6 Drawing Sheets

HEATED CATHETER FOR MONITORING CARDIAC OUTPUT

TECHNICAL FIELD

This invention generally pertains to a method and apparatus for controlling the temperature of a heated catheter, and more specifically, to controlling the temperature of a catheter used in determining cardiac output.

BACKGROUND OF THE INVENTION

Cardiac output, the volumetric rate at which blood is pumped through the heart, is most often determined clinically by injecting a bolus of chilled saline or glucose solution into the heart through a catheter. A thermistor inserted in the blood at a point downstream of the heart as the chilled injectate/blood mixture is pumped from the heart, is used to determine a temperature-time washout curve; the area under this curve provides an indication of cardiac output. Although this thermo-dilution method can give an indication of cardiac output at the time the procedure is performed, it cannot be used for continuously monitoring cardiac output. The frequency with which the procedure is performed is limited by its adverse effects on a patient, including the dilution of the patient's blood that occurs each time the chilled fluid is injected. In addition, the procedure poses an infection hazard to medical staff from blood contact, and to the patient from contaminated injectate fluid or syringes.

An analogous method for measuring cardiac output involves the injection of a heated fluid into the heart; however, the same limitations on the frequency with which the measurement can be performed exist, whether the injectate is heated or chilled. Alternatively, blood in the heart can be chilled or heated by a heat transfer process using a temperature conditioned fluid that is circulated down one lumen within the catheter and returned back through another lumen. The principal advantages of using such a non-injectate heat transfer process to change the temperature of blood are that the blood is not diluted, and the temperature differential between the heat exchanger and the blood is reduced, compared to the differential temperature between an injectate fluid and blood in the typical thermal dilution method. U.S. Pat. No. 4,819,655 discloses an injectateless method and apparatus for determining cardiac output in this fashion.

Another technique for changing the temperature of blood circulating through the heart in order to determine cardiac output uses an electrical resistive heater that is disposed on the catheter and heated by an electrical current that is carried by conductors that run through one or more lumens in the catheter. A constant average power dissipation is typically maintained in the resistive heater, thereby enabling cardiac output to be determined as a simple function of the power dissipated and the temperature rise of blood measured downstream of the resistive heater. Several patents issued to H. Khalil, including U.S. Pat. Nos. 3,359,974, 4,217,910, and 4,240,441, disclose various catheters and monitoring systems for carrying out this procedure.

A disadvantage in maintaining a constant power dissipation in the resistive heater used in the preceding technique results from variations in the surface temperature of the heater as the rate of flow of blood past the heater changes. At relatively low rates of flow, the surface temperature of the catheter around the resistive heater can rise to a level at which damage to blood cells can occur. In addition, as the catheter is initially inserted into a patient's vascular system, care must be taken to turn off the electrical current used to heat the resistive heater, since the absence of a cooling blood flow can cause the resistive heater to become hot enough to burn when it is outside the body. To avoid damaging the blood or burning the patient in this manner, the maximum power dissipated in the heating element is severely limited. The temperature increase in blood flowing past the resistive heater at higher rates of flow is thus minimal, and as a result, the temperature change of the blood measured downstream is relatively low. This condition produces a poor signal-to-noise ratio at high volumetric flow rates, since the signal indicating temperature rise of the blood downstream of the heating element varies as the reciprocal of blood flow rate.

Previously Newbower (E. Trautman, R. Newbower, "The Development of Indicator Dilution Techniques", I.E.E.E. Trans. BME-31 No. 12 December 1984, pp. 800–807; R. Newbower et al., "Continuous Electronic Thermal Dilution Measurements," in Proc. 29th A CEMB, Boston, Mass., 1976) concluded that within the safety constraints noted above, heated catheter based thermal dilution could not be used in most patients clinically, because of poor signal-to-noise ratio with the limited safe maximum power.

Accordingly, it is an object of the present invention to provide a system for heating blood to determine cardiac output that avoids the limitations of prior art constant power dissipation systems, without creating a potential hazard of damaging blood cells by overheating or burning the patient. These and other objects and advantages of the present invention will be apparent by reference to the attached drawings and the Description of the Preferred Embodiments that follows.

SUMMARY OF THE INVENTION

Apparatus comprising the present invention is used for heating blood flowing through a heart in order to determine cardiac output based upon a temperature rise of the blood. This apparatus includes a resistive heater that is connectable to a source of electrical current and is mounted on a catheter body that is adapted to be inserted intravascularly into the heart, the heater being mounted some distance from the catheter's distal end. Temperature sensing means are provided for sensing the temperature of the resistive heater and for producing a signal indicative of that temperature. Control means are connected to receive the signal indicative of the temperature of the resistive heater and are operative to control the electrical current flowing from the source through the resistive heater so that the temperature of the resistive heater does not exceed a predetermined value.

In one form of the invention, the temperature sensing means comprise a temperature sensor that is mounted in thermal communication with the resistive heater so as to sense its temperature. In another embodiment, a resistance of the resistive heater varies with its temperature, and the temperature sensing means include a plurality of resistors connected in a bridge circuit with the resistive heater. The control means operate to control the electrical current flowing through the resistive heater as a function of a potential developed across the bridge circuit.

Alternatively, the temperature sensing means can comprise means for measuring the electrical current flowing through the resistive heater and a voltage drop across it. The signal indicative of the temperature of the resistive heater is then proportional to the ratio of the voltage drop and the electrical current flowing through the resistive heater (the resistive heater having a resistance that varies with temperature).

In another form of the invention, the control means are operative to generally maintain a nominal, fixed power dissipation in the resistive heater, but reduce the electrical current flowing through the resistive heater to establish a different nominal fixed power dissipation if the temperature of the resistive heater otherwise exceeds the predetermined value. The control means can include means for producing a reference signal corresponding to the predetermined value and a comparator connected to compare the signal indicative of the temperature of the resistive heater to the reference signal to produce an output signal corresponding to their difference. The output signal of the control means is used to control the electrical current flowing through the resistive heater. In addition, the apparatus can include means for measuring the electrical power dissipated in the resistive heater as a function of the signal indicative of its temperature for use in determining the cardiac output.

A method for protecting blood and tissue from damage due to overheating caused by heat transfer from a catheter used to monitor cardiac output comprises a further aspect of this invention. The method includes the steps of monitoring the temperature of a heated portion of the catheter and producing a signal indicative of that temperature. In response to the signal, the temperature of the heated portion is controlled to prevent it from exceeding a predetermined maximum safe level. The signal indicative of temperature is then used in determining power dissipated to heat the blood, which is used in determining cardiac output. The step of monitoring the temperature comprises the steps of measuring an electrical current flowing through a resistive heater and measuring a voltage drop across the resistive heater. The temperature of the heated portion of the catheter is then proportional to a ratio of the voltage drop and the electrical current. Alternatively, the step of monitoring the temperature comprises the step of monitoring a potential difference developed across the output from a bridge circuit in which the resistive heater is one part of the bridge circuit.

DESCRIPTION OF THE PREFERRED EMBODIMENTS

Figure 1:
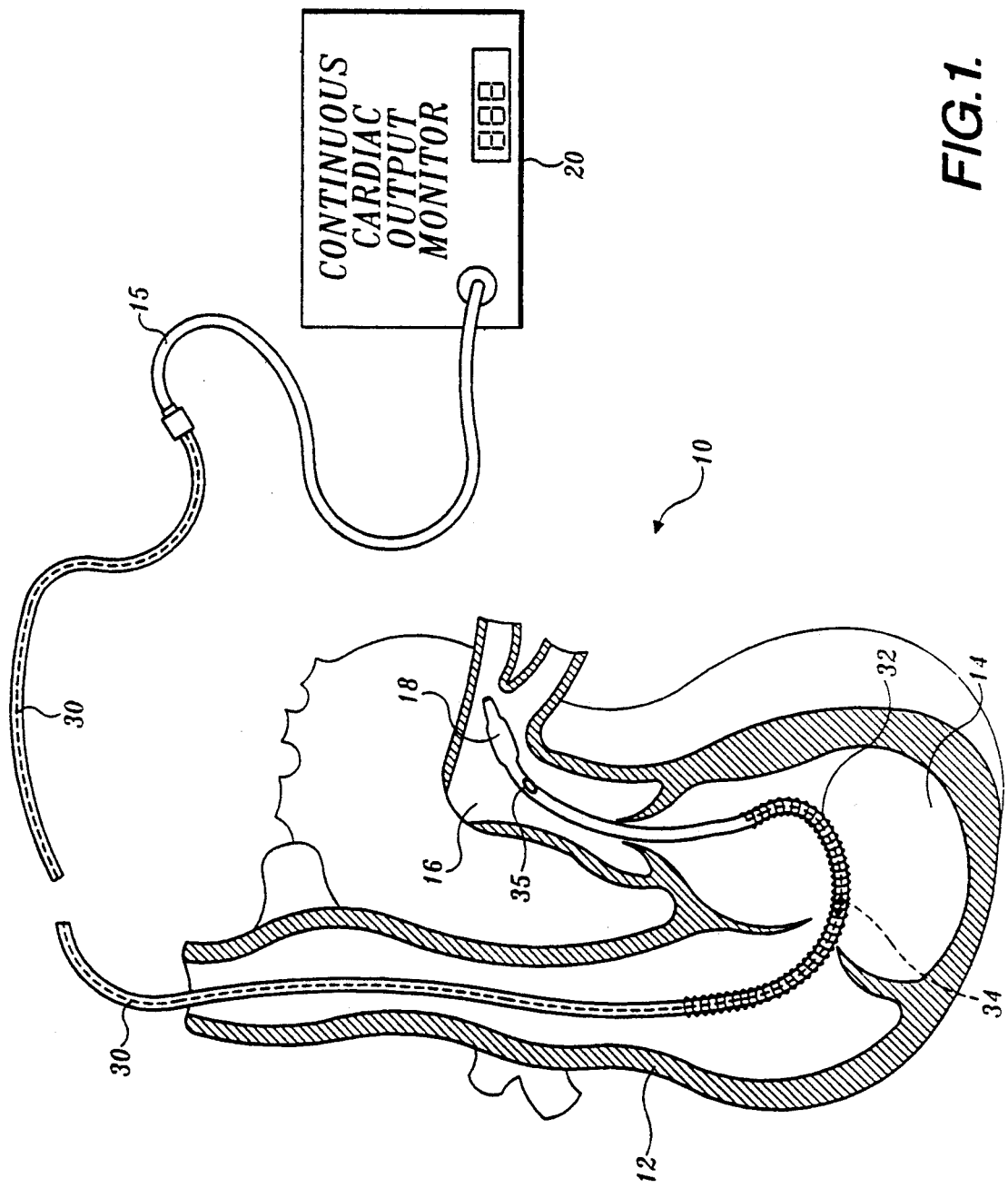
FIG. 1 is a cross-sectional stylized view of a heart muscle showing the use of a heated catheter to continuously monitor cardiac output in accordance with the present invention.

FIG. 1 is a cross-sectional, stylized view of a heart muscle 10, showing the use of a heated catheter 30 to continuously monitor cardiac output in accordance with the present invention. The heated catheter 30 is shown after it has been inserted intravascularly into a right atrium 12 and extending into a right ventricle 14. A balloon 18 is inflated to carry the distal end of the heated catheter into pulmonary artery 16. Disposed upon heated catheter 30 is a resistive heater 32, mounted so that it is set back from a distal end of heated catheter 30. As shown in the embodiment of FIG. 1, the heater 32 is set back about 15 cm from the distal end of heated catheter 30. Resistive heater 32 preferably comprises a coiled wire of copper or other electrically conductive material, and is about 15 cm long in the preferred embodiment. Heated catheter 30 is connectable to a continuous cardiac output monitor 20 via a lead 15, which provides an electrical current to resistive heater 32. The heating current is usually made to vary between zero and some predetermined maximum value in a repetitive fashion. As blood flows into right ventricle 14, its temperature is increased by resistive heater 32. Turbulence in the right ventricle ensures thorough mixing of the heated blood adjacent to the heated catheter, with the new blood entering the right ventricle before the heated blood is pumped out into pulmonary artery 16. The conventional method of determining the volumetric flow rate of blood being pumped by heart muscle 10 is by monitoring the amount of power that is dissipated in resistive heater 32 and the corresponding temperature rise of the blood leaving the heart due to this added heat. The temperature rise varies inversely with flow rate. A distal temperature sensor 34 that is disposed at the distal end of heated catheter 30 determines the temperature rise of the blood in the pulmonary artery 16. Use of a repetitive or continuously varying heating power waveform rather than a fixed heating power allows the blood temperature rise due to heating to be discriminated from naturally occurring blood temperature fluctuations and drift.

In the preferred embodiment, cardiac output monitor 20 can include a microprocessor (not shown) that is capable of computing cardiac output as a function of the temperature rise of the blood and the power dissipated in resistive heater 32. As discussed above, when determining cardiac output using a heated catheter, the temperature of the resistive heater may become sufficiently high to damage red blood cells as blood within heart muscle 10 is heated, due to a low rate of flow of blood through the heart. Conversely, if the power dissipation of resistive heater 32 is set sufficiently low to avoid overheating blood cells during low rates of flow, the signal-to-noise ratio may be too low to accurately measure high rates of flow when the temperature signal becomes very small. Also, if electrical current is inadvertently applied to heated catheter 30 before it is inserted into the patient's vascular system, the patient may be burned during the insertion procedure because the blood is not flowing past resistive heater 32 to cool it.

The present invention controls the temperature of resistive heater 32 so as to prevent injury, while insuring an adequate signal is provided.

Figure 2A:
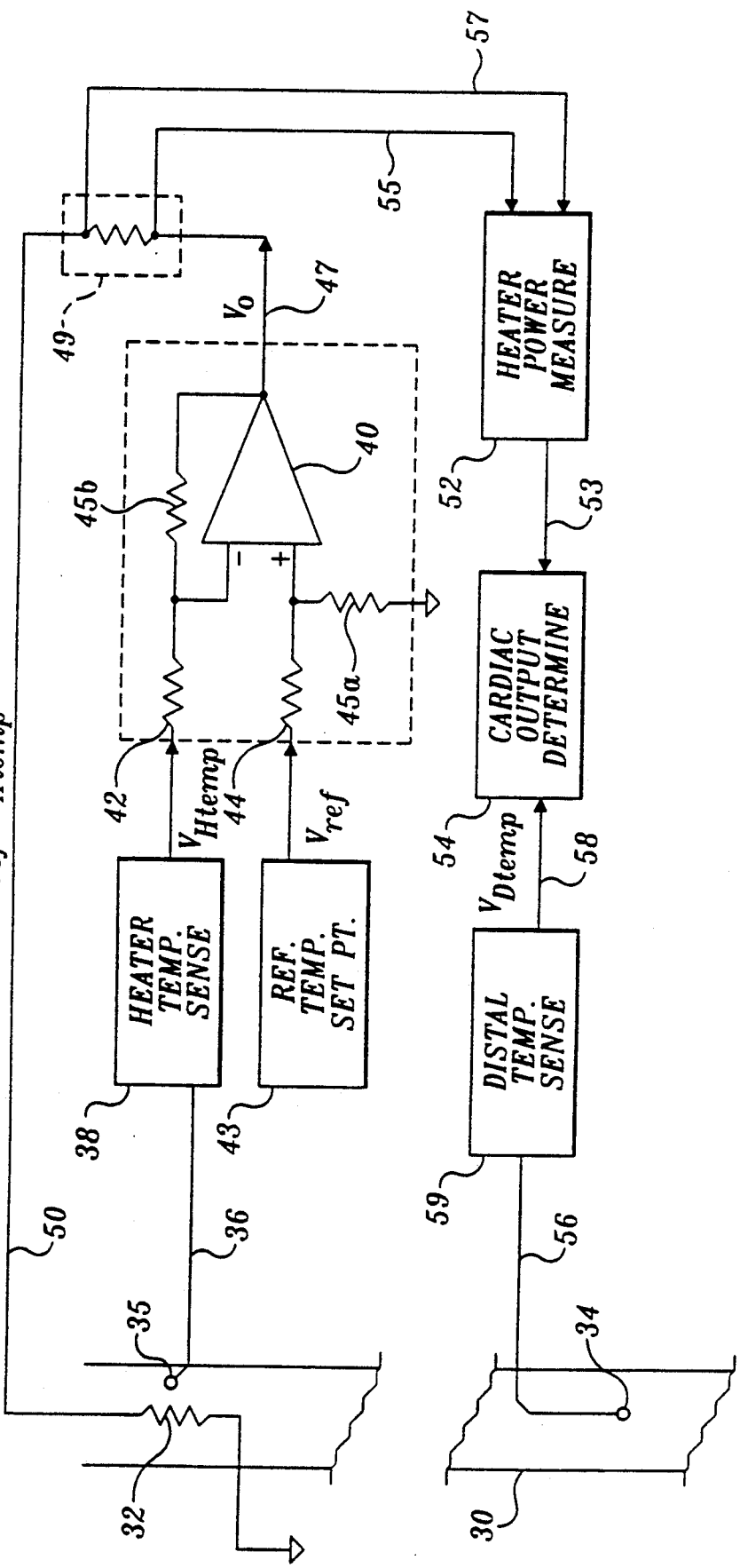
FIG. 2A is a schematic block diagram showing a first embodiment of means for sensing the temperature of a heated portion of the catheter and maintaining a constant temperature using a voltage source.
Figure 2B:
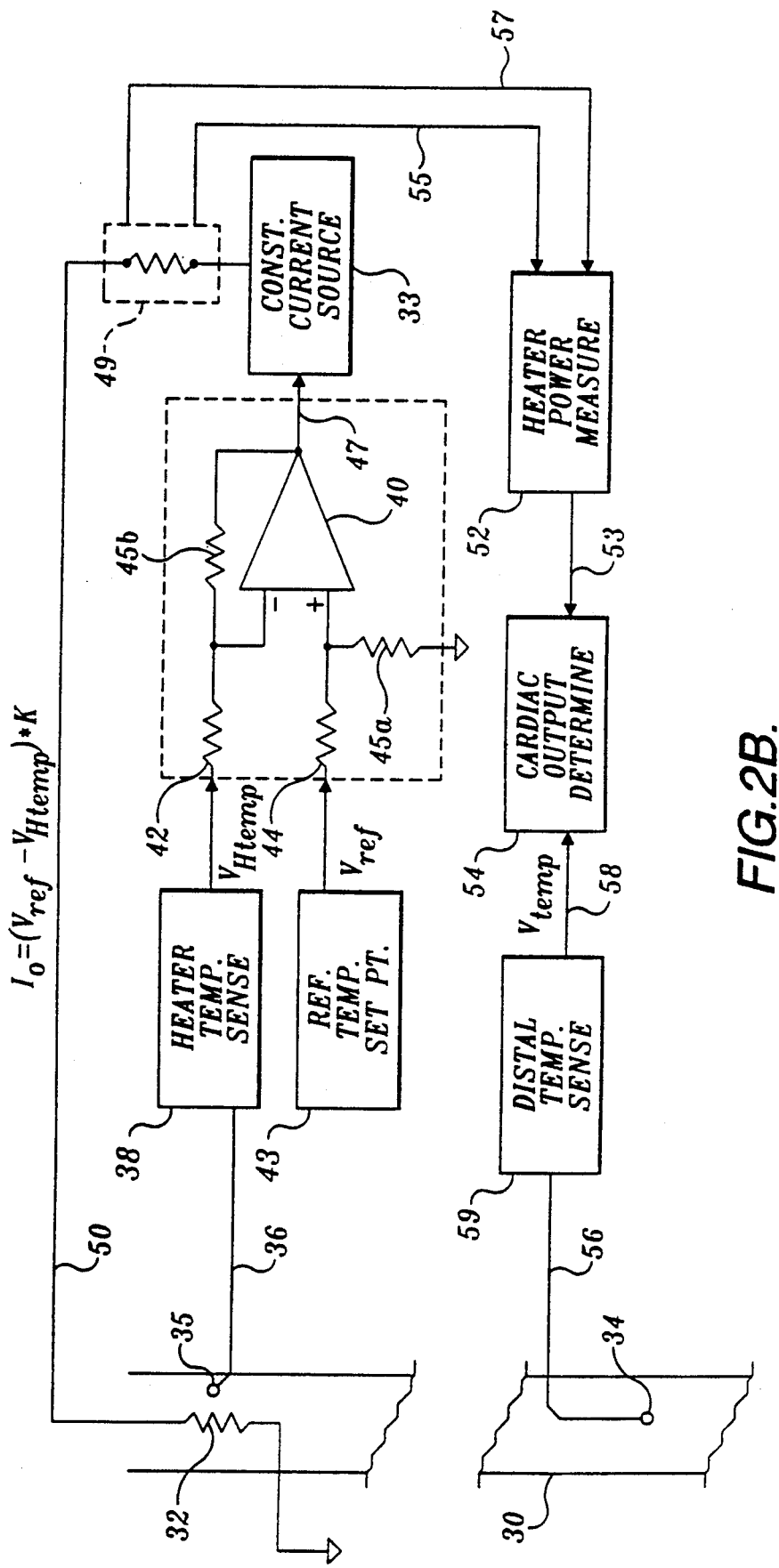
FIG. 2B is a schematic block diagram showing a second embodiment of the present invention, which is driven by a constant current source, but otherwise similar to the first embodiment of FIG. 2A.

FIGS. 2A and 2B are schematic block diagrams showing a first embodiment of means for sensing the temperature of resistive heater 32 on heated catheter 30. A temperature sensor 35 (e.g., a thermistor) is disposed adjacent resistive heater 32 and is connected by a lead 36 to a temperature sensing signal conditioning block 38. (In FIG. 1, temperature sensor 35 has a dash tag line to indicate that it is not required in several embodiments of this invention.) Signal conditioning block 38 converts a signal from temperature sensor 35 to an output signal $V_{Htemp}$, that is proportional to the temperature of resistive heater 32. A reference temperature block 43 provides a signal, $V_{ref}$, that is proportional to a predetermined maximum temperature above which the temperature of resistive heater 32 should not rise. Blood is sensitive to elevated temperatures, and damage to red blood cells can occur even at relatively low temperatures if such temperature exposure is for a substantially long period of time. Accordingly, the signal $V_{ref}$ is preferably set to correspond to a reference temperature selected to avoid damage at the temperature and duration selected.

Signal conditioning block 38 is connected to an inverting input terminal of a differential amplifier 40 via an input resistor 42, and reference temperature or set point block 43 is connected to a noninverting input terminal of differential amplifier 40 via an input resistor 44. A resistor 45a is connected between the noninverting input and ground, and a feedback resistor 45b is connected between the output and inverting input of differential amplifier 40. Differential amplifier 40 amplifies the difference between the signals $V_{Htemp}$ and $V_{ref}$ by a gain, K, to produce a voltage $V_o$, as follows:

$$V_o = (V_{ref} - V_{Htemp}) * K \quad (1)$$

This voltage $V_o$ causes a current $I_o$ to flow through a lead 47 to a current sensor 49, and through heater 32 via a lead 50. Current sensor 49 has a very low resistance so that a voltage drop across the heater (heater voltage), $V_{htr}$, substantially equals $V_o$.

In FIG. 2B, a second embodiment is illustrated that is the same as the first embodiment of FIG. 2A, except that the voltage $V_o$ is applied through lead 47 to a constant current source 33. This voltage controls the constant current source so that it generates a constant current $I_o$ defined as follows:

$$I_o = (V_{ref} - V_{Htemp}) * K \quad (2)$$

The current $I_o$ flows through current sensor 49 into heater 32 via lead 50.

If the heater temperature should rise above the level set by reference temperature block 43, the heater voltage $V_{htr}$ (in the embodiment of FIG. 2A) or current $I_o$ (in the embodiment of FIG. 2B) falls causing less power to be dissipated in resistive heater 32, with a corresponding reduction in its temperature. Correspondingly, if the heater temperature should fall below the level set by reference temperature block 43, the heater voltage $V_{htr}$ (in the embodiment of FIG. 2A) or current $I_o$ (in the embodiment of FIG. 2B) rises causing more power to be dissipated in resistive heater 31 with a corresponding increase in temperature. This feedback arrangement thus maintains the temperature of resistive heater 32 substantially at the predetermined temperature set by reference temperature block 43.

In both the first and the second embodiments, current sensor 49 is connected to a power measurement block 52 and provides a signal over leads 55 and 57 proportional to the heater current $I_o$. In addition, lead 57 also carries the heater voltage, $V_{htr}$, as an input to the power measurement block. Power measurement block 52 determines the amount of power dissipated in resistive heater 32 from the product of voltage drop across the heater, $V_{htr}$, and the current through the heater, $I_o$. A signal indicative of the power dissipated in resistive heater 32 is supplied from power measurement block 52 to a cardiac output determining block 54 via a lead 53.

A lead 56 that extends through heated catheter 30 connects temperature sensor 34 to a distal temperature sensing block 59. Temperature sensing block 59 provides a signal indicative of the temperature rise of the blood downstream from resistive heater 32, due to heat from resistive heater 32, to cardiac output determination block 54 via a lead 58.

Based on the signals indicative of the temperature rise of the blood provided via lead 58 and the power dissipated in resistive heater 32 provided via lead 53, cardiac output determination block 54 determines the volumetric rate of blood flow from heart muscle 10 for both the first and second embodiments.

Figure 3A:
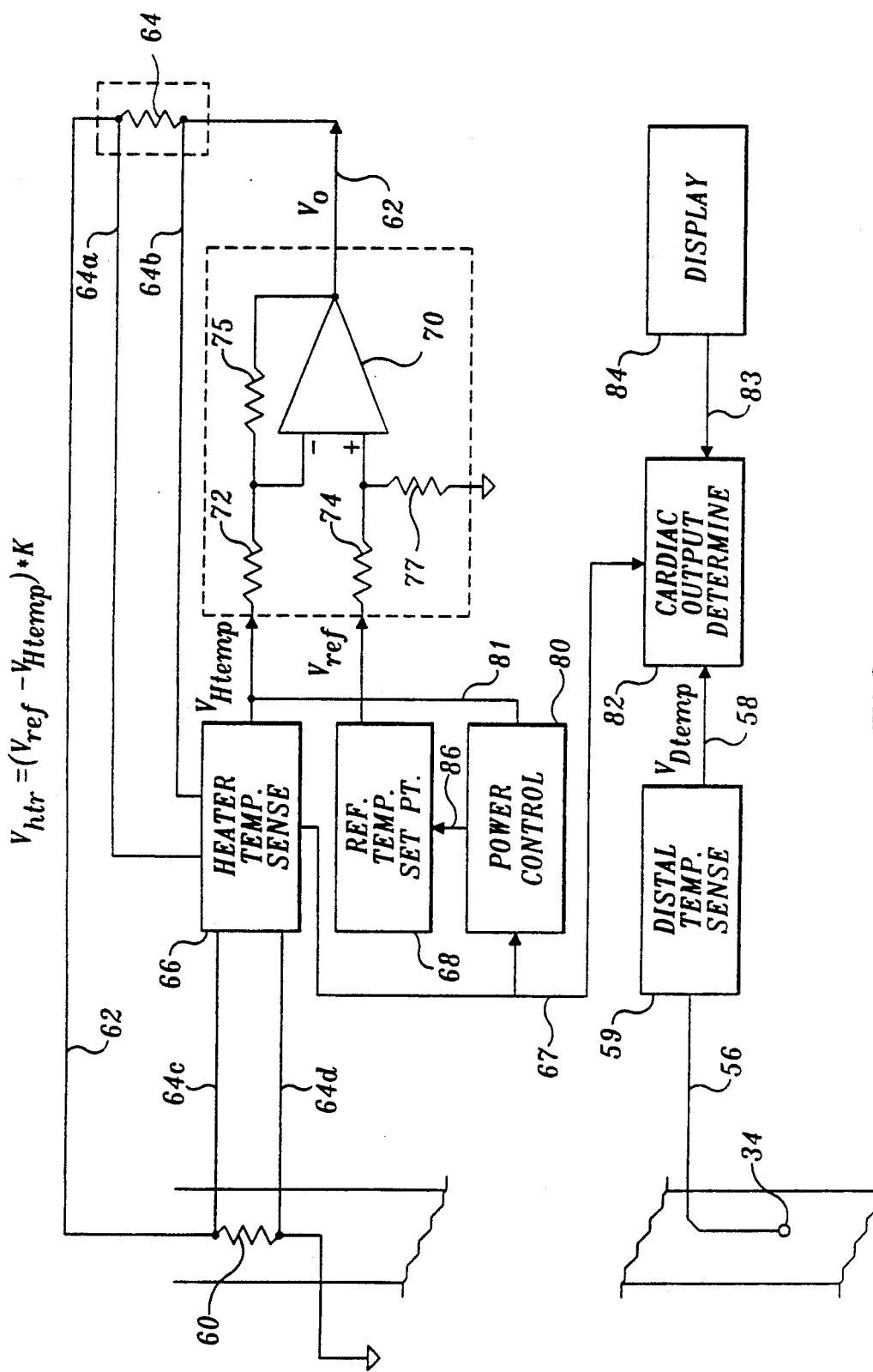
FIG. 3A is a schematic block diagram showing a third embodiment of means for sensing the temperature of the heated portion of the catheter.

FIG. 3A shows a third embodiment of the heated catheter system according to the present invention. A resistive heater 60 has a characteristic resistive temperature coefficient (RTC) that varies significantly in a well defined manner with temperature. Resistive heater 60 receives an electric current from a differential amplifier 70 via a lead 62. Connected in series between resistive heater 60 and the output of differential amplifier 70 is a current sensor 64, having a resistance, $R_S$. By measuring a voltage drop, $E_S$ across current sensor 64, a signal conditioning and processing block 66 determines the level of current flowing through the current sensor 64 and hence, through resistive heater 60. This heater current, $I_{htr}$, is determined from the ratio $E_S/R_S$. Signal conditioning and processing block 66 receives the voltage drop signal $E_S$ over leads 64a and 64b, and a signal indicative of the heater voltage, $V_{htr}$, i.e., the voltage across resistive heater 60, via leads 64c and 64d, which are connected at opposite ends of resistive heater 60. Signal conditioning and processing block 66 then determines the temperature of resistive heater 60 as a function of its resistance, which is obtained from the ratio of $V_{htr}/I_{htr}$, as well as the power dissipated in the heater from the product, $V_{htr} \times I_{htr}$.

An output signal of signal conditioning and processing block 66, $V_{Htemp}$, is proportional to the temperature of resistive heater 60; this output signal is connected to an inverting input terminal of differential amplifier 70 via a resistor 72. A reference block 68 provides a signal, $V_{ref}$, corresponding to a predetermined temperature at which resistive heater 60 is to be maintained. In a fourth embodiment shown in FIG. 3B, reference block 68 provides a signal, $V_{ref}$, corresponding to a variable reference for controlling the power dissipated in resistive heater 60. In either case, reference block 68 is connected to a noninverting input terminal of differential amplifier 70 via a resistor 74. The output of differential amplifier 70 is connected to lead 62, which carries the electrical current that heats resistive heater 60. A feedback resistor 75 is connected between lead 62 and the inverting input of the differential amplifier. A resistor 77 connects the noninverting input of the differential amplifier to ground. The output signal of differential amplifier 70 is thus proportional to $V_{ref} - V_{Htemp}$.

Referring to the embodiment of FIG. 3A, lead 81 connects the $V_{Htemp}$ signal from signal conditioning and processing block 66 to a power control block 80. Power control block automatically controls the signal $V_{ref}$ as explained below.

During use of the heated catheter, power control block 80 receives a signal on a lead 67 from signal conditioning and processing block 66 that is proportional to the power being dissipated by resistive heater 60. In this embodiment of the invention (FIG. 3A) a generally constant power dissipation is maintained in resistive heater 60. Accordingly, power control block 80 compares the signal indicative of power dissipation in resistive heater 60 with a predefined setpoint power dissipation. Power control block 80 produces a control signal that is conveyed to reference block 68 over a lead 86 that adjusts the $V_{ref}$ signal so that the setpoint power dissipation is achieved and maintained. However, should the temperature of resistive heater 60 exceed a predefined maximum value, power control block 80 sends a control signal to reference block 68 over lead 86 that incrementally decreases the power dissipation being maintained in resistive heater 60, by adjusting the $V_{ref}$ signal. After a predefined time interval, e.g., 20 seconds, power control block 80 again adjusts the $V_{ref}$ signal to incrementally decrease the power dissipation in resistive heater 60 if its temperature still exceeds the predefined maximum value. Power control block 80 also incrementally increases the power dissipated in resistive heater 60 if its temperature drops below a predetermined minimum level. So long as the temperature of resistive heater 60 remains between the predetermined minimum and maximum levels, power control block 80 produces a control signal that maintains a constant power dissipation in the resistive heater.

Figure 3B:
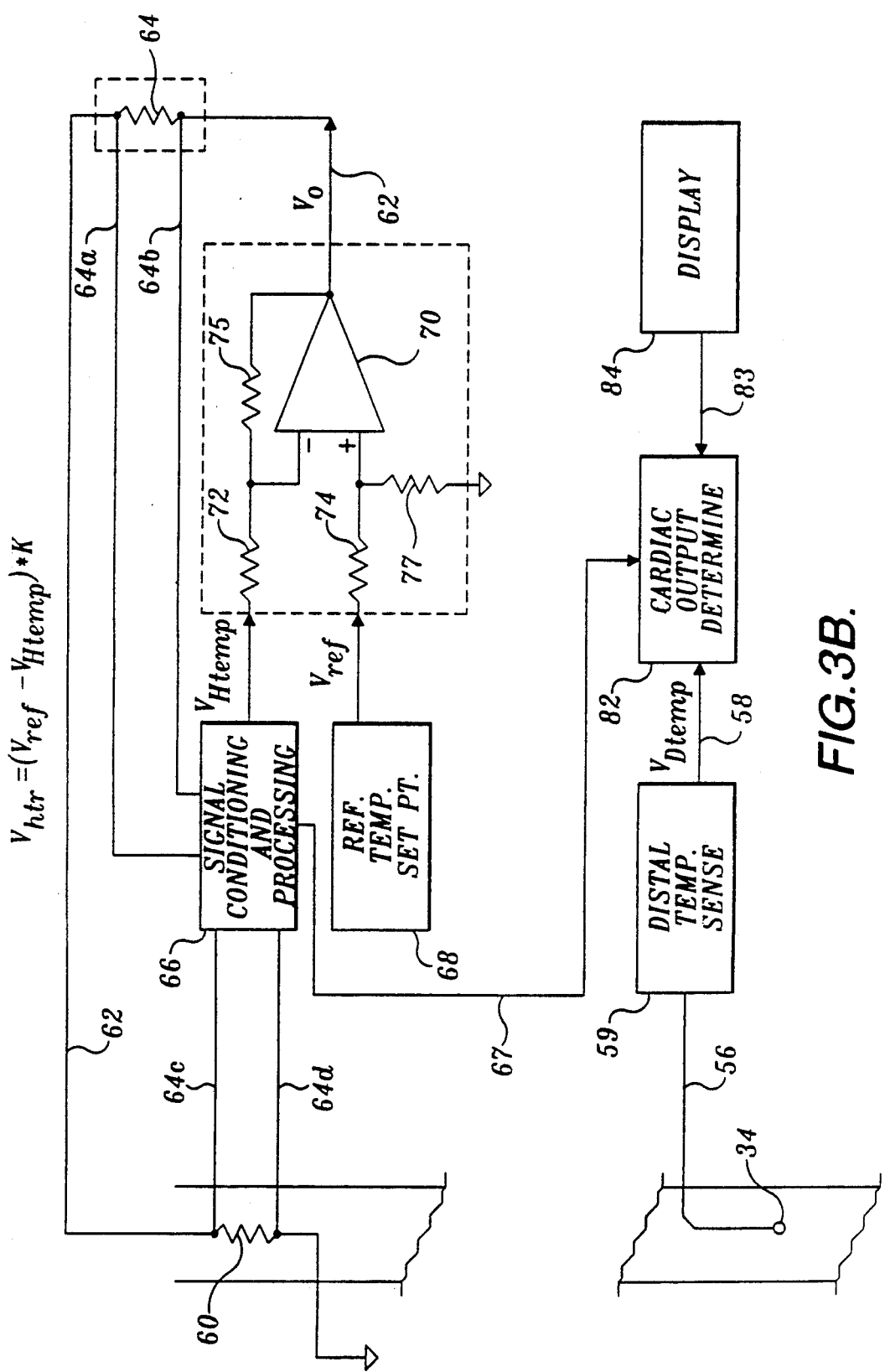
FIG. 3B is a schematic block diagram showing a fourth embodiment, similar in many respects to the third embodiment of FIG. 3A.

In the embodiment shown in FIG. 3B, power control block 80 is not required (and is therefore omitted), and reference block 68 simply provides a $V_{ref}$ signal corresponding to the predetermined temperature at which resistive heater 60 is to be maintained. Differential amplifier 70 then produces an output current that varies so as to maintain the predetermined temperature.

For both of the embodiments of FIGS. 3A and 3B, cardiac output determination block 82 is connected to receive the $V_{Htemp}$ signal over lead 67 and determines the cardiac output of the heart muscle based on the temperature of resistive heater 60, $V_{Htemp}$, the power dissipated by it, and the temperature of the blood downstream, as described above. A display 84 is connected to cardiac determination block 82 by leads 83 to provide a visual indication of the cardiac output of the heart muscle.

Figure 4:
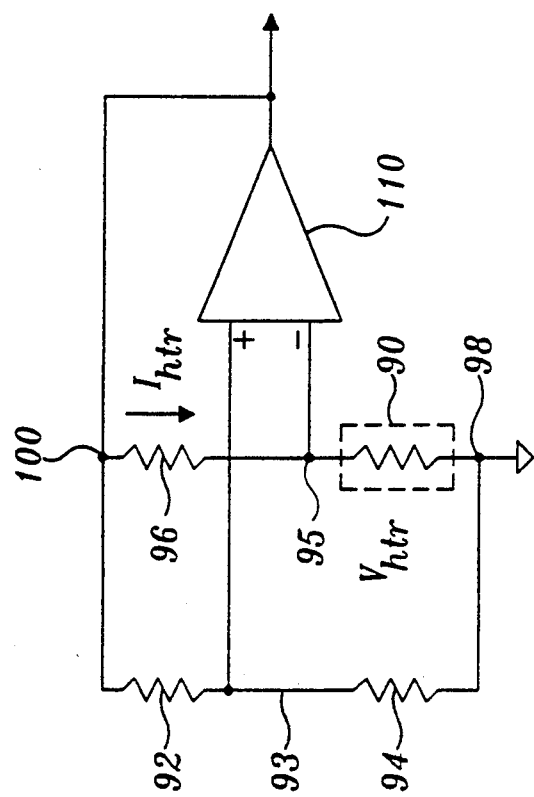
FIG. 4 is a schematic block diagram showing a fifth embodiment of means for sensing the temperature of the heated portion of the catheter.

FIG. 4 shows yet another embodiment of the present invention. A resistive heater 90 is chosen for its characteristic resistance that varies significantly with temperature. Resistive heater 90 comprises one arm of a bridge circuit 85 that also includes three fixed resistors 92, 94, and 96. Resistors 92 and 94 are connected in series at a node 93 to form the left side of the bridge circuit, while resistor 96 and resistive heater 90 are connected in a series at a node 95 to form the right side of the bridge circuit. Resistor 94 and resistive heater 90 are connected to ground at a node 98, while resistor 92 and resistor 96 are connected to a node 100 through which an electrical current is supplied to the bridge circuit. Connected to the bridge circuit is a differential amplifier 110 having an inverting input terminal, which is connected to node 95 and a noninverting input terminal, which is connected to node 93. The output of differential amplifier 110 is connected to supply current to node 100 of the bridge circuit 85.

When a resistive heater 90 with a positive temperature coefficient is used, and if resistive heater 90 is initially cold, its resistance is relatively low; consequently, bridge circuit 85 is unbalanced, and the signal applied to the inverting input terminal of differential amplifier 110 is at a substantially different potential than the signal applied to its noninverting input terminal. Because the output signal of differential amplifier 110 is proportional to the difference between its inputs, the output signal causes an electrical current that is proportional to the different input of differential amplifier 110 to flow through the bridge circuit. This electrical current causes resistive heater 90 to become warm. As the temperature of resistive heater 90 increases, its resistance rises until the voltage on bridge circuit output, node 95, which is applied to the inverting input of differential amplifier 110, rises to a level where it almost exactly matches the bridge output voltage applied to the noninverting input, at node 93, causing the differential amplifier output voltage to fall and reducing the heating current in resistive heater 90. If the voltage gain of differential amplifier 110 is high, the output voltage at node 100 settles to a value at which the heat dissipated in the resistive heater 90 just causes the bridge to balance with only a very small differential input to the differential amplifier 110. Any increased cooling of the resistive heater due to increased heat transfer to the blood causes the resistance of resistive heater 90 to decrease and changes the differential input voltage to differential amplifier 110. This change in input voltage causes the differential amplifier output applied to node 100 to rise, keeping the bridge balanced and the differential amplifier input low, by increasing power dissipation in resistive heater 90. Conversely, decreased cooling of resistive heater 90 due to decreased heat transfer to the blood causes the heater resistance to fall and the amplifier output applied to node 100 to fall, keeping the bridge balanced and the amplifier differential input low. Differential amplifier 110 and bridge circuit 85 thus cooperate to keep resistive heater 90 at the predetermined constant resistance and hence at a predetermined constant temperature determined by the resistance values selected for resistors 92, 94, and 96, and the characteristic resistance of resistive heater 90.

Power dissipation in resistive heater 90 is determined generally as explained above in respect to the embodiments of FIGS. 3A and 3B. Specifically, the voltage drop across resistor 96 is monitored between nodes 95 and 100, to determine the current, $I_{htr}$, through resistive heater 90, and the voltage drop across the resistive heater, $V_{htr}$, is determined between nodes 95 and 98 (ground). The power dissipated is thus simply the product of $I_{htr}$ and $V_{htr}$.

Although the preceding description has been directed to the preferred embodiments of the invention, those skilled in the art will realize that changes thereto can be made without departing from the spirit and scope of the invention as defined by the following claims. Therefore, the scope of the invention should be determined solely by reference to the claims.

The embodiments of the invention in which an exclusive property or privilege is claimed are defined as follows:

1. Apparatus for heating blood flowing through a heart in order to determine cardiac output based upon a temperature rise of the blood, comprising:
   (a) a resistive heater connectable to a source of electrical current;
   (b) a catheter having a distal end that can be inserted intravascularly into the heart the distal end including a temperature sensor for sensing the temperature of blood heated by the resistive heater, the resistive heater being mounted on the catheter and displaced from the distal end thereof so that the temperature sensor is not directly affected by the temperature of the resistive heater;
   (c) temperature sensing means, for sensing the temperature of the resistive heater and producing a signal indicative thereof; and
   (d) control means, connected to receive the signal indicative of the temperature of the resistive heater, for controlling an electrical current flowing from the source through the resistive heater so that the temperature of the resistive heater does not exceed a predetermined value.

2. The apparatus of claim 1, wherein the temperature sensing means comprise a temperature sensor that is mounted in thermal communication with the resistive heater so as to sense its temperature.

3. The apparatus of claim 1, wherein the resistive heater has a resistance that varies with temperature, and wherein the temperature sensing means includes a plurality of resistors connected in a bridge circuit with the resistive heater, the control means responding to a potential developed across the bridge circuit to control the electrical current flowing through the resistive heater.

4. The apparatus of claim 1, wherein the control means are operative to maintain a nominal fixed power dissipation in the resistive heater, but reduce the electrical current flowing through the resistive heater to establish a different nominal fixed power dissipation if the temperature of the resistive heater otherwise exceeds the predetermined value.

5. The apparatus of claim 1, further comprising means for measuring electrical power dissipated in the resistive heater as a function of the signal indicative of its temperature, producing a signal corresponding thereto for use in determining the cardiac output.

6. Apparatus for use in continuously monitoring cardiac output based upon a temperature rise of blood flowing through a heart due to heat transfer, comprising:
   (a) a catheter having a distal end and a temperature sensor disposed proximate the distal end;
   (b) means for supplying heat to a heated portion of the catheter, heat transfer from the heated portion of the catheter serving to heat the blood within the heart, the heated portion being displaced from the distal end of the catheter so that the temperature sensor disposed proximate the distal end of the catheter can sense the temperature of blood heated by the means for supplying heat without being directly affected by the temperature of said means;
   (c) temperature sensing means for monitoring the temperature of the heated portion of the catheter, producing a signal indicative thereof; and
   (d) control means, connected to receive the signal indicative of the temperature of the heated portion of the catheter, for controlling the temperature of the heated portion so that it does not rise to a level likely to damage the blood.

7. The apparatus of claim 6, wherein the temperature sensing means comprise a temperature sensor disposed at the heated portion of the catheter so as to monitor its temperature.

8. The apparatus of claim 6, wherein the means for supplying heat dissipate a nominally fixed power in the heated portion of the catheter and the control means are operative to vary the temperature of the heated portion, thereby causing a different nominally fixed power to be dissipated only if the temperature of the heated portion rises above the level likely to damage the blood.

9. Apparatus for heating blood flowing through a heart in order to determine cardiac output based upon a temperature rise of the blood, comprising:
   (a) a resistive heater connectable to a source of electrical current, wherein the resistive heater has a resistance that varies with temperature;
   (b) a catheter having a distal end that can be inserted intravascularly into the heart, the resistive heater being mounted on the catheter and displaced from a distal end thereof;
   (c) temperature sensing means, for sensing the temperature of the resistive heater and producing a signal indicative thereof, wherein the temperature sensing means comprise means for measuring an electrical current flowing from the source through the resistive heater and a voltage drop across the resistive heater, and
   (d) control means, connected to receive the signal indicative of the temperature of the resistive heater, for controlling the electrical current flowing from the source through the resistive heater so that the temperature of the resistive heater does not exceed a predetermined value, wherein the signal indicative of the temperature of the resistive heater is proportional to a ratio of the voltage drop across the resistive heater and the electrical current flowing through the resistive heater.

10. The apparatus of claim 9, wherein the controls means include for producing a reference signal corresponding to the predetermined value and a comparator connected to compare the signal indicative of the temperature of the resistive heater to the reference signal, producing an output signal corresponding to their difference that is used to control the electrical current flowing through the resistive heater.

11. Apparatus for heating blood flowing through a heart in order to determine cardiac output based upon a temperature rise of the blood, comprising:
   (a) a resistive heater connectable to a source of electrical current;
   (b) a catheter having a distal end that can be inserted intravascularly into the heart, the resistive heater being mounted on the catheter and displaced from distal end thereof;
   (c) temperature sensing means, for sensing the temperature of the resistive heater and producing a signal indicative thereof;
   (d) control means, connected to receive the signal indicative of the temperature of the resistive heater, for controlling the electrical current flowing from the source through the resistive heater so that the temperature of the resistive heater does not exceed a predetermined value; and (e) means for measuring electrical power dissipated in the resistive heater as a function of the signal indicative of its temperature, producing a signal corresponding thereto for use in determining the cardiac output.

12. Apparatus for use in continuously monitoring cardiac output based upon a temperature rise of blood flowing through a heart due to heat transfer, comprising:
(a) a catheter;
(b) means for supplying heat to a heated portion of the catheter, heat transfer from the heated portion of the catheter serving to heat the blood within the heart, wherein the means for supplying heat comprise a resistive heater disposed at the heated portion of the catheter, the resistive heater adapted to be connected to a source of an electrical current and having a resistance that varies with temperature;
(c) temperature sensing means for monitoring the temperature of the heated portion of the catheter, producing a signal indicative thereof, wherein the temperature sensing means comprise means for measuring an electrical current flowing through the resistive heater and a voltage drop across it, the signal indicative of the temperature of the heated portion being proportional to a ratio of the voltage drop and the electrical current; and
(d) control means, connected to receive the signal indicative of the temperature of the heated portion of the catheter, for controlling the temperature of the heated portion so that it does not rise to a level likely to damage the blood.

13. Apparatus for heating blood flowing through a heart in order to determine cardiac output based upon a temperature rise of the blood, comprising:
(a) a resistive heater connectable to a source of an electrical current, the resistive heater having a resistance that varies with its temperature;
(b) a catheter having a distal end that can be inserted intravascularly into the heart the distal end including a temperature sensor for sensing a temperature of blood heated by the resistive heater, the resistive heater being mounted on the catheter and displaced from the distal end thereof so that the temperature sensor is not directly affected by the temperature of the resistive heater;
(c) temperature sensing means, for sensing the temperature of the resistive heater and producing a signal indicative thereof, wherein the temperature sensing means comprise means for measuring the electrical current flowing through the resistive heater and a voltage drop across it, and wherein the signal indicative of the temperature of the resistive heater is proportional to a ratio of the voltage drop and the electrical current flowing through the resistive heater; and
(d) control means connected to receive the signal indicative of the temperature of the resistive heater, for controlling the electrical current flowing from the source through the resistive heater so that the temperature of the resistive heater does not exceed a predetermined value.

14. Apparatus for heating blood flowing through a heart in order to determine cardiac output based upon a temperature rise of the blood, comprising:
(a) a resistive heater connectable to a source of an electrical current;
(b) a catheter having a distal end that can be inserted intravascularly into the heart the distal end including a temperature sensor for sensing a temperature of blood heated by the resistive heater, the resistive heater being mounted on the catheter and displaced from the distal end thereof so that the temperature sensor is not directly affected by a temperature of the resistive heater;
(c) temperature sensing means, for sensing the temperature of the resistive heater and producing a signal indicative thereof; and
(d) control means, connected to receive the signal indicative of the temperature of the resistive heater, for controlling the electrical current flowing from the source through the resistive heater so that the temperature of the resistive heater does not exceed a predetermined value, wherein the control means include means for producing a reference signal corresponding to the predetermined value and a comparator connected to compare the signal indicative of the temperature of the resistive heater to the reference signal, producing an output signal corresponding to their difference that is used to control the electrical current flowing through the resistive heater.

15. Apparatus for use in continuously monitoring cardiac output based upon a temperature rise of blood flowing through a heart, comprising:
(a) a catheter having a heater mounted thereon:
(b) means for supplying heat to the heater that is insertable intravascularly into a heart, heat transfer from the heater serving to heat the blood within the heart, wherein the means for supplying heat comprise a source of an electrical current coupled electrically to the heater so that the electrical current flows through the heater, and wherein said heater has a resistance that varies with its temperature;
(b) temperature sensing means for monitoring the temperature of the heater, producing a signal indicative thereof; and
(c) control means, connected to receive the signal indicative of the temperature of the heater, for controlling the temperature of the heater so that it does not rise to a level likely to damage the blood.

16. The apparatus of claim 15, wherein the temperature sensing means comprise means for measuring the electrical current flowing through the heater and a voltage drop across it, the signal indicative of the temperature of the heated portion being proportional to a ratio of the voltage drop and the electrical current.

17. The apparatus of claim 15, wherein the temperature sensing means comprise a resistance network that includes the resistive heater and means for sensing voltage differential across the resistance network to produce the signal indicative of the temperature of the heated portion.

18. The apparatus of claim 17, the electrical heating current flowing through the resistive heater provides the signal indicative of the temperature of the heated portion of the catheter.

* * * * *

UNITED STATES PATENT AND TRADEMARK OFFICE
CERTIFICATE OF CORRECTION

PATENT NO. : 5,277,191
DATED : January 11, 1994
INVENTOR(S) : T. J. Hughes

It is certified that error appears in the above-indentified patent and that said Letters Patent is hereby corrected as shown below:

| COLUMN | LINE | |
|---|---|---|
| 10 | 24 | "a" should read --the-- |
| 10 | 43 | "controls" should read --control-- |
| 10 | 44 | after "include" insert --means-- |

Signed and Sealed this

Thirty-first Day of May, 1994

Attest:

BRUCE LEHMAN

Attesting Officer

Commissioner of Patents and Trademarks